Figure 1:
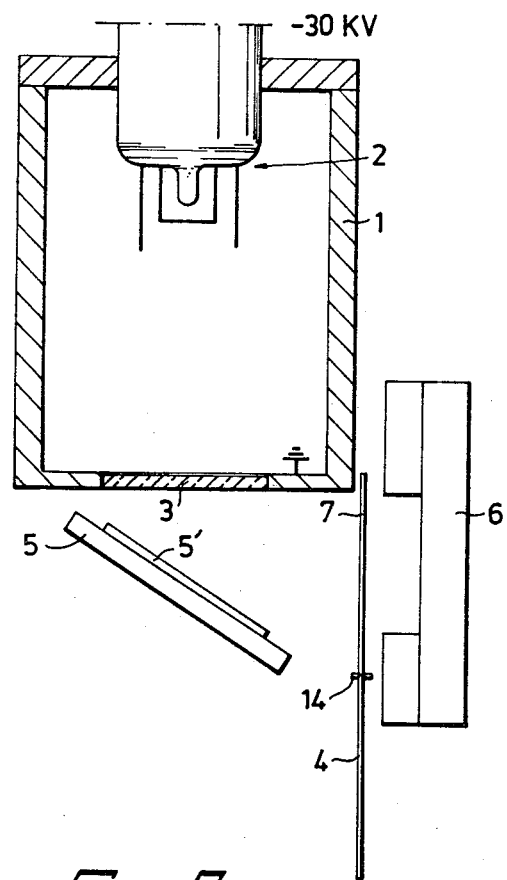

United States Patent [19]

Baecklund

[11] 4,344,181

[45] Aug. 10, 1982

[54] METHOD AND APPARATUS FOR MEASURING THE CONTENT OR QUANTITY OF A GIVEN ELEMENT BY MEANS OF X-RAY RADIATION

[76] Inventor: Nils J. Baecklund, Sunnevik, Oskarshamn, Sweden, S-572 00

[21] Appl. No.: 214,862

[22] Filed: Dec. 9, 1980

Related U.S. Application Data

[63] Continuation of Ser. No. 48,232, Jun. 13, 1979, abandoned.

[30] Foreign Application Priority Data

Jun. 21, 1978 [SE] Sweden ............................. 7807078

[51] Int. Cl.³ ............................................ G01N 23/22
[52] U.S. Cl. ......................................... 378/45; 378/157
[58] Field of Search ............ 250/272, 273, 274, 277 R

[56] References Cited

U.S. PATENT DOCUMENTS

| | | | |
|---|---|---|---|
| 2,999,937 | 9/1961 | Kohler | 250/272 |
| 3,732,426 | 5/1973 | Shoemezer | 250/272 |
| 3,963,922 | 6/1976 | Zulliger | 250/272 |
| 4,048,496 | 9/1977 | Albert | 250/272 |

Primary Examiner—Craig E. Church
Attorney, Agent, or Firm—Larson and Taylor

[57] ABSTRACT

A method and apparatus for measuring the content of an element by means of X-ray-radiation. Electrons from the cathode of a low-power X-ray tube are directed onto one side of the anode of said tube, said anode comprising a thin layer of anode material on a beryllium plate. The electrons excite primary X-ray-radiation in the anode material, including the characteristic X-ray lines. The radiation passes out through the opposite side of the anode as transmission radiation and is directed onto the element to be measured, whereupon fluorescense occurs, said fluorescense being caused by the characteristic lines. The fluorescense lines of the substance are then isolated by means of a balanced filter.

4 Claims, 2 Drawing Figures

METHOD AND APPARATUS FOR MEASURING THE CONTENT OR QUANTITY OF A GIVEN ELEMENT BY MEANS OF X-RAY RADIATION

This is a continuation of application Ser. No. 048,232 filed June 13, 1979 now abandoned.

The present invention relates to a method and an apparatus for measuring the content or quantity of a given element in a sample by means of X-ray-radiation. The apparatus includes a low-power X-ray tube, having, for example, a power output of some tens of watts; a power-supply source; a sample holder; and a measuring device.

Apparatus of the aforedescribed kind used for measuring the contents of elements and including a conventional high-power X-ray tube are previously known. In such known apparatus, a wave-length range which excites in the best mode the element whose content is to be measured is filtered out from white X-ray-radiation. The fluorescense radiation occurring when the element in question is excited, is reflected from the examined sample and caused to pass through a further filter in which the lines in the fluorescense radiation characteristic of the element in question are filtered out.

Although the aforedescribed known apparatus has many advantages and has been widely used in practice, it has the disadvantage that a large part of the power used does not cause excitation in the sample. Thus, it is necessary to use an X-ray tube of about 400 W and hence the apparatus requires a good supply of electrical current and intermittent operation, or the provision of cooling devices.

Apparatus which include a specifically constructed low-power X-ray tube are also known. In one such apparatus there is used a thin tungsten anode which is arranged such that the electrons impinge on one side thereof and the X-ray-radiation exits from the other side. The excitation voltage and the anode material are selected such as to obtain white X-ray-radiation. radiation. All of the white radiation impinges on the sample, and radiation reflected from the sample is divided up with a conventional spectograph having a flat crystal. This apparatus has not found use in practice, because the intensities of the instrument are low and its measuring accuracy consequently poor.

An object of the present invention is to provide a method and an apparatus in which characteristic lines, which have wave lengths which are shorter than an absorption edge of the element to be measured, of sufficient purity is excited and filtered by the anode of the X-ray tube, and in which the intensity of the X-ray source is maintained within a large solid angle, and in which the fluorescence line of the element to be measured is filtered out with a balanced filter.

The characterizing features of the method and the apparatus according to the invention are disclosed in the characterizing clauses of respective claims.

The invention will now be described in more detail with reference to an exemplary embodiment of an apparatus according to the invention illustrated in the accompanying drawing, in which FIG. 1 shows schematically the main parts of an X-ray tube in the apparatus according to the invention, and a sample holder and a measuring device.

Figure 2:
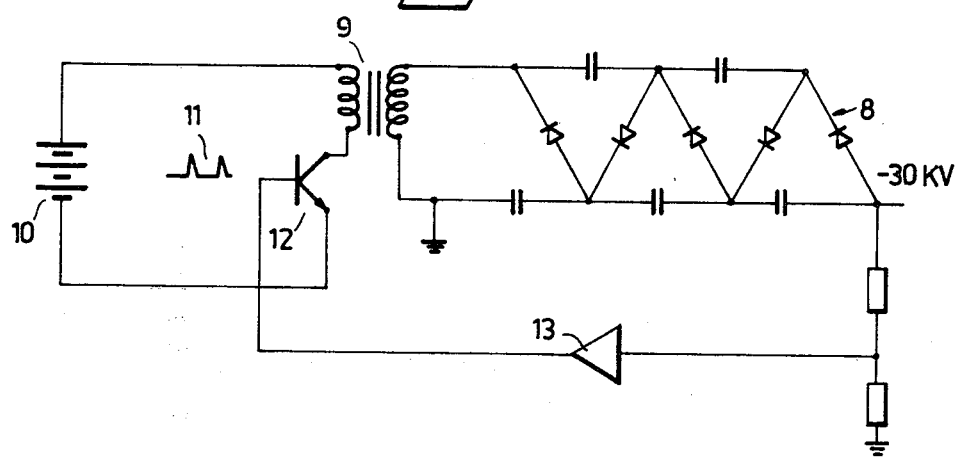

FIG. 2 illustrates the current-supply unit of the X-ray tube shown in FIG. 1.

In an apparatus according to the invention the characteristic radiation from a suitably selected anode material is used to excite the element to be measured in the best mode. In order to obtain the characteristic radiation with the highest possible yield and the highest possible freedom of choice in anode material, the X-ray tube is designed for low power with anodes of the transmission type, i.e. the electron radiation is caused to impinge on one side of the anode and the X-ray radiation used is taken out from its other side. This use of the transmission anode enables practically half the solid angle within which the X-radiation is transmitted to be used. In conventional X-ray tubes only one or two hundredths of this solid angle are used, and in the previously mentioned apparatus having a transmission anode, this advantage has not been availed upon at all.

Those skilled in this particular art usually maintain that there are only a few substances which can be used as anodes in X-ray tubes, but as a result of the design of a low-power tube having a high radiation yield with a transmission anode according to the invention it is possible to lower the anode temperature and by, for example, using a window of beryllium coated with a desired material as the anode, there is obtained efficient cooling and high electrical conductivity, thereby greatly increasing the number of substances from which the anode material can be selected. By using as the carrier a material which is only slightly absorbent to X-ray-radiation, such as beryllium, even material having very low melting point, such as gallium ($+30°$ C.) can be used as anode material.

The transmission anode affords an important advantage in the generation of substantially monochromatic X-ray-radiation with an electron energy which only slightly exceeds the energy required in order for the monochromatic radiation to be excited. Incident electrons are retarded at a very small depth—about 0.5 $\mu$m—and when retarded produce a white, so-called continuous spectrum. This continuous spectrum extends practically unhindered on the side on which the radiation impinges. The said radiation is absorbed, however, in the transmission direction and its short-wave part is converted to characteristic radiation. Thus, there is obtained pure radiation in the transmission direction.

The X-ray tube illustrated in FIG. 1 comprises a casing 1, a cathode 2 and an anode 3, said anode also forming a window in the wall of the casing. Below the window, i.e. in this embodiment the anode, and in line with the cathode there is arranged a sample holder 5 on which the sample 5' to be examined rests. Arranged parallel with the X-ray tube on one side thereof is a measuring device 6, such as a GM-gube, which receives radiation from the sample 5' through a filter 4,7. This filter is a so-called balanced filter and comprises two filter elements 4 and 7 of two different elements with absorption edges at different wavelength but with the same absorption properties for wavelengths which are shorter and longer than the absorption edge of the shortest wave and the longest wave respectively. The filter elements can be swung alternately in front of the window of the measuring device 6 about a pivot 14.

In FIG. 2 there is illustrated an exemplary embodiment of a current-supply device whose output is connected to the cathode of the X-ray tube, and which comprises a voltage converter which provides $-30$ KV on said output. The main parts of the said device comprise a cascade coupling 8, a transformer 9 and a D.C. battery 10 which may comprise, for example, a conventional dry battery or accumulator. The battery voltage is applied to the primary winding of the transformer 9, causing current pulses 11 to be sent through a transistor 12. The control pulses of the transistor are obtained from a pulse generator not shown. In the secondary winding of the transformer amplified voltage pulses are obtained which give rise on the output of the coupling 8 to a constant continuous voltage of up to $-30$ KV which is applied to the cathode of the X-ray tube. A feedback from the output occurs to the base of the transistor 12 via an amplifier 13 to control the current through the transistor in a manner such as to maintain the high voltage constant.

The novel and essential feature of the X-ray tube shown in FIG. 1 is the anode 3, which is a transmission anode, i.e. the electrons from the cathode 2 impinge on the anode on one side thereof (in FIG. 1 the upper side) whilst the excited primary X-ray-radiation is received on the other side of said anode (in FIG. 1 the underneath of said anode). The anode comprises a thin layer of a well-defined anode material on a beryllium plate having characteristic X-ray lines $K_\alpha$ and $K_\beta$ having a somewhat shorter wavelength than the corresponding characteristic X-ray lines $K_\alpha$ and $K_\beta$ of the element in the sample 5' to be measured. Thus, there is chosen an anode material which provides a line which passes the substance in the sample to be measured, for example a chromium anode when the quantity or content of titanium in a sample is to be measured.

One advantage obtained when using transmission radiation instead of conventional reflected radiation is that, by using a relatively low excitation voltage on the cathode there can be obtained a purer radiation. The short-wave radiation (in form of a continuous spectrum) is absorbed in the anode material and gives rise to characteristic lines in the transmission radiation. A further advantage is that the anode can comprise the window of the X-ray tube, thereby enabling the distance between the anode and the sample to be kept short and the solid angle within the sample is irradiated to be kept high. Both of these factors greatly influence the intensity, and the design provides a significant increase in said intensity.

The primary characteristic X-ray emission through the window produces fluorescense in the element to be measured, the intensity of the characteristic fluorescense lines reflected from the sample 5' being measured by means of the GM-tube 6. The primary characteristic X-ray-radiation is also absorbed, however, in the sample 5' and if the sample is thin or is in gas or liquid form, the absorption band can be measured behind the sample, i.e. beneath the sample holder 5, and the content or quantity of the element in question can be determined.

An X-ray tube according to the invention also greatly widens the range for radioactive isotopes with an X-ray-radiation and may also replace these, rendering them unnecessary.

It has long been known to those skilled in this particular art that the excitation of fluorescense radiation and the measurement of absorption properties is best effected with monochromatic or substantially monochromatic radiation. The reason why practically all work within these ranges is today effected with white X-ray-radiation or with wave-length ranges filtered out from white X-ray radiation is mainly because the X-ray technique has been developed towards higher powers and because it has been considered within the art unreasonable to utilize other anode materials than those few having a high melting point and a high thermal conductivity.

Among those advantages afforded by a monochromatic X-ray source of suitable wave-length can be included:

(a) extremely high fluoroescense yield
(b) an almost monochromatic background
(c) selective excitation—only the line or lines which have a longer wave-length than the primary radiation can be excited.

These properties combine well with filter techniques for isolating an X-ray line in fluorescense analysis and absorption analysis.

Thus, it is surprising to those skilled in this art to discover that with a low-power X-ray source in which the anode material can be selected from a far wider range of anode materials than with high-power sources, and with a combination of known filter techniques, there is provided a novel system for X-ray fluorescense analysis and absorption analysis of small dimensions and small power requirement.

The technical advance afforded by the invention will be apparent, inter alia, from measurements which have been taken, in which the intensity of large conventional instruments has been compared with the intensity of the low-power system according to the invention.

| Spectrograph | Element | Sample | Power | Intensity per % |
|---|---|---|---|---|
| Philips | Mn | Stainless steel | 1 kW | 9.700 imp/S |
| ARL | Cr | Stainless steel | 2 kW | 11.000 imp/S |
| ARL | Ni | Stainless steel | 2 kW | 8.700 imp/S |
| According to the invention | Cr | Stainless steel | 2 W | 12.000 imp/S |
| According to the invention | Mn | Stainless steel | 2 W | 13.000 imp/S |

Thus, the invention enables the content of a substance to be measured by means of a battery-operated apparatus just as quickly and as positively as the large stationary instruments.

The method according to the invention can also be carried out with the use of a low-power X-ray tube having two anodes or with two low-power X-ray tubes in which the radiation is caused to pass through the sample and the anode materials are so selected that the characteristic radiation of one anode is of shorter wave-length than the absorption edge of the predetermined substance and the characteristic radiation of the other anode is of somewhat longer wave-length than said edge. The radiation of longer wave-length passing through the sample is used to control a neutral wedge-shaped filter arranged in the radiation path or to control the power of the two X-ray tubes in a manner such that the radiation of longer wave-length constantly passes with the same intensity with different types of samples and different sample thicknesses and the intensity of the radiation of shorter wave-length is measured subsequent to passing through the sample.

I claim:

1. A method of measuring the content or amount of a given element in a sample by means of X-ray radiation comprising the steps of:

utilizing a low-power X-ray tube having an anode fabricated of anode material with characteristic X-ray lines of substantially equal to but shorter waver-length than the corresponding characteristic X-ray lines of the element to be measured, the anode comprising a thin layer of said anode material coated on a beryllium plate of a characteristic such as to provide efficient cooling;

utilizing a battery as the power supply for said low-power X-ray tube;

causing electrons from a cathode of the low-power X-ray tube to be directed onto one side of the anode of the tube such that the electrons excite primary X-ray radiation in the anode material including the radiation from the characteristic X-ray lines of the anode material;

causing the X-ray lines of the anode material, taken out as transmission radiation through the opposite side of the anode and including characteristic radiation having a wave-length which is shorter than the absorption edge of the given element, to impinge on the sample containing the element to be measured thereby generating X-ray lines characteristic of the sample by fluorescence;

isolating the characteristic fluorescence lines of the given element from the fluorescence radiation of the sample by means of two filter elements having absorption edges which lie at different wave-lengths but which have the same absorption properties for those wave-lengths which are shorter than the shortest wave-length absorption edge of the two filter elements and for those wave-lengths which are longer than the longest wave-length absorption edge of the two filter elements, respectively; and measuring the intensity of the characteristic X-ray lines of the element to determine the content or amount of the element, the intensity in the part of the spectrum lying between the absorption edges of the filters being determined by subtracting the intensity obtained by the filter element having the absorption edge of longer wave-length from the intensity obtained with the filter element having the absorption edge of shorter wavelength.

2. An apparatus for carrying out a method of measuring the content or amount of a given element in a sample by means of X-ray radiation, said element producing characteristic X-ray lines when irradiated with X-radiation, said apparatus including a low-power X-ray tube, a battery operated power supply for said low-power X-ray tube and a sample holder, said apparatus further comprising a combination of an anode in the X-ray tube which comprises a thin layer of an anode material coated on a beryllium plate of a characteristic such as to provide efficient cooling and having characteristic X-ray lines $K_{60}$ and $K_\beta$ which are substantially equal to but shorter wave-length than the corresponding characteristic X-ray lines of the element to be measured, the cathode of said X-ray tube being located on one side of the anode and the sample holder with the sample on the other side of said anode outside a window in the X-ray tube such that only X-ray-radiation transmitted through the anode is directed against the sample, a filter means for receiving fluorescence radiation from the sample, said filter means comprising two filter elements of different elements having absorption edges at different wave-lengths but having the same absorption ability with respect to wave-lengths which are shorter than the shortest wave-length absorption edge of the two filter elements and those wave-lengths which are longer than the longest wave-length absorption edge of the two filter elements and means for measuring the intensity of the characteristic X-ray lines of the element to determine the content or amount of the element, by subtracting the intensity obtained by the filter element having the absorption edge of longer wavelength from the intensity obtained with the filter element having the absorption edge of shorter length, so as to determine the intensity in the part of the spectrum lying between the absorption edges of the filters.

3. An apparatus according to claim 2, characterized in that the anode comprises the window of said X-ray tube.

4. An apparatus according to claim 2 or claim 3, characterized in that the measuring device includes a gas discharge tube.

* * * * *